US008784474B2

(12) United States Patent
Sargent, Jr.

(10) Patent No.: US 8,784,474 B2
(45) Date of Patent: Jul. 22, 2014

(54) EMERGENCY VASCULAR REPAIR SYSTEM AND METHOD (75) Inventor: Peter W. Sargent, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 357 days.

(21) Appl. No.: 13/091,697

(22) Filed: Apr. 21, 2011

(65) Prior Publication Data
US 2012/0271402 A1 Oct. 25, 2012

(51) Int. Cl.
A61F 2/06 (2013.01)

(52) U.S. Cl.
CPC ........................................ A61F 2/064 (2013.01)
USPC ............................................ 623/1.15; 623/1.23

(58) Field of Classification Search
CPC .............. A61F 2/06; A61F 2/064; A61F 2/90
USPC .................... 623/1.15, 1.2, 1.3, 1.36
See application file for complete search history.

(56) References Cited

U.S. PATENT DOCUMENTS

| 5,405,378 | A | * | 4/1995 | Strecker | 623/1.12 |
|---|---|---|---|---|---|
| 5,609,628 | A | | 3/1997 | Keranen | 623/1 |
| 5,776,186 | A | | 7/1998 | Uflacker | 623/1 |
| 5,941,908 | A | * | 8/1999 | Goldsteen et al. | 623/1.23 |
| 6,315,792 | B1 | | 11/2001 | Armstrong et al. | 623/1.23 |
| 6,346,118 | B1 | | 2/2002 | Baker et al. | 623/1.12 |
| 6,514,281 | B1 | | 2/2003 | Blaeser et al. | 623/1.12 |
| 6,773,456 | B1 | | 8/2004 | Gordon et al. | 623/1.28 |
| 7,252,680 | B2 | | 8/2007 | Freitag | 623/1.12 |
| 7,527,645 | B2 | | 5/2009 | Perez et al. | 623/1.23 |
| 2003/0208263 | A1 | | 11/2003 | Burmeister et al. | 623/1.19 |
| 2005/0119722 | A1 | | 6/2005 | Styrc et al. | 623/1.12 |
| 2006/0025852 | A1 | | 2/2006 | Armstrong et al. | 623/1.17 |
| 2007/0027526 | A1 | | 2/2007 | Demetriades et al. | 623/1.13 |

* cited by examiner

Primary Examiner — Kathleen Holwerda
Assistant Examiner — Sarah Simpson
(74) Attorney, Agent, or Firm — Brinks Gilson & Lione (57) ABSTRACT A system to deliver a prosthesis for repair of a transected body vessel is described herein. The system can have a prosthesis and a plurality of distinct strands. A releasable loop can be formed at a distal end of each strand and positioned to retain one of a plurality of portions of the prosthesis in a compressed configuration. Each portion of the prosthesis can be independently movable between the compressed configuration and an expanded configuration. Retraction of the proximal end or severing the loop of any one of the strands can cause the corresponding loop to release to allow the corresponding portion of the prosthesis to expand from the compressed configuration to the expanded configuration. The prosthesis can couple two vessel portions of the transected vessel together to allow for blood perfusion and maintain hemostasis.

17 Claims, 6 Drawing Sheets

EMERGENCY VASCULAR REPAIR SYSTEM AND METHOD

BACKGROUND

The present disclosure relates generally to medical devices for emergency repair of body vessels. More particularly, it relates to systems for deploying prostheses used for repairing damaged body vessels and gaining hemostasis during emergency medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be rapidly performed at great speed, and with a high degree of physician skill. Such treatments may occupy an undue amount of time and attention of the trauma physician at a time when other pressing issues regarding the patient's treatment require immediate attention. In addition, the level of partidularized skill required to address a vascular trauma may exceed that possessed by the typical trauma physician. Particularly, traumatic episodes to the vessel may require the skills of a physician specially trained to address the particular vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures, and the blood flow is more quickly restored and damage caused by lack of blood flow is minimized.

Trauma physicians generally find it difficult to manipulate a prosthesis for insertion into a body vessel that has been traumatically injured. For example, one difficulty arises from the trauma physician trying to limit the size of the opening created for gaining access to the injured vessel so that such opening requiring healing is as small as possible. Another difficulty is that the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible. Yet, a small portion removed from the vessel leaves such a small space between the two vessel portions, thereby making it difficult to introduce the prosthesis between the two vessel portions.

Thus, what is needed is a treatment system for delivering a prosthesis for use in repair of an injured body vessel, such as an artery or a vein, (and in particular a transected vessel) during emergency surgery. It would be desirable if such treatment system is easy for a trauma physician to use, and can rapidly introduce a prosthesis into two vessel portions of a transected vessel, thereby providing a conduit for blood within the injured body vessel.

SUMMARY

Accordingly, a system is provided herein to address at least some of the shortcomings of the prior art. The system can be used for open surgical repair of a transected body vessel. In one example, the system can include a prosthesis having at least two portions. The prosthesis can be movable between a compressed configuration and an expanded configuration. Each of the portions of the prosthesis can be retainable in the compressed configuration independently of the other portion. The system further can include first and second strands. The first strand can have a proximal end and a distal end. The distal end of the first strand can include a first releasable loop. The first releasable loop can surround one of the portions of the prosthesis to retain the portion of the prosthesis in the compressed configuration. The second strand can have a proximal end and a distal end. The distal end of the second strand can include a second releasable loop. The second releasable loop can surround the other portion of the prosthesis to retain the other portion of the prosthesis in the compressed configuration. The first and/or second releasable loops can be configured to be removed in response to retraction of the proximal end of the corresponding strand from external to the prosthesis to allow for expansion of the corresponding portion of the prosthesis to the expanded configuration to engage a vessel portion. One strand may have a tensile strength less than the tensile strength of the other strand such that the other strand can withstand a greater proportion of the outward radial force exerted by the prosthesis. The first and second strands may be disposed on the outer ends of the prosthesis or may be disposed on one side of the prosthesis such as an outer end and an intermediate portion of the prosthesis. The first and second strands may be disposed exterior to a body of the prosthesis so that the proximal ends of the first and second strands can converge toward a middle of the prosthesis and can be externally accessible from the middle of the prosthesis. Anchoring members can be disposed on the prosthesis for vessel fixation and to prevent migration of the prosthesis.

In another example, the system can include first and second outer strands and first and second inner strands. Each strand can have a proximal end and a distal end. The distal end of each of the strands can include a releasable loop. The releasable loop of each of the first and second outer strands and the first and second inner strands can surround the first and second outer ends of the prosthesis and the first and second intermediate portions of the prosthesis, respectively, to retain the respective portion in the compressed configuration. The proximal end of each of the first outer strand, the first inner strand, the second outer strand, and the second inner strand can be disposed external to the prosthesis so that the proximal ends of the strands converge toward a middle of the prosthesis and are externally accessible from the middle of the prosthesis. The first outer end of the prosthesis is configured to be positioned within a first vessel portion and the second outer end of the prosthesis is configured to be positioned within a second vessel portion such that release of each of the releasable loops from the prosthesis allows for expansion thereof within the vessel portions. The loops can be released by various mechanisms such as retraction of the proximal ends of the strands or by severing the loops of the strands. The strands can be released to minimize or completely eliminate any portion of the strands from remaining in the body after expansion of the prosthesis.

In yet another example, a method of connecting first and second vessel portions of a transected body vessel during open surgery is provided. A first outer end of a prosthesis retained in a compressed configuration by a first releasable loop of a first strand can be inserted into the end opening of the first vessel portion. The proximal end of the first strand can be retracted from external to the prosthesis to release the first releasable loop from the first outer end of the prosthesis to permit expansion of the first outer end of the prosthesis to engage a wall of the first vessel portion. A second outer end of the prosthesis retained in a compressed configuration by a second releasable loop of a second strand can be inserted into the end opening of the second vessel portion. The proximal end of the second strand can be retracted from external to the prosthesis to release the second releasable loop from the second outer end of the prosthesis to permit expansion of the second outer end of the prosthesis to engage a wall of the second vessel portion. The expanded prosthesis can couple the first and second vessel portions together to form a continuous flow path therebetween.

DETAILED DESCRIPTION OF THE DRAWINGS AND THE PRESENTLY PREFERRED EMBODIMENTS

For the purposes of promoting an understanding of the principles of the present disclosure, reference will now be made to the embodiments illustrated in the drawings, and specific language will be used to describe the same. The system described herein can be useful for repair of a body vessel, such as a blood vessel, during an emergency open surgical procedure. This system can be particularly useful to deploy a prosthesis for repair of a lacerated artery or vein during emergency open surgery, and particularly, to obtain hemostasis while maintaining blood perfusion. Other applications for the system will become readily apparent to one skilled in the art from the detailed description.

Figure 1:
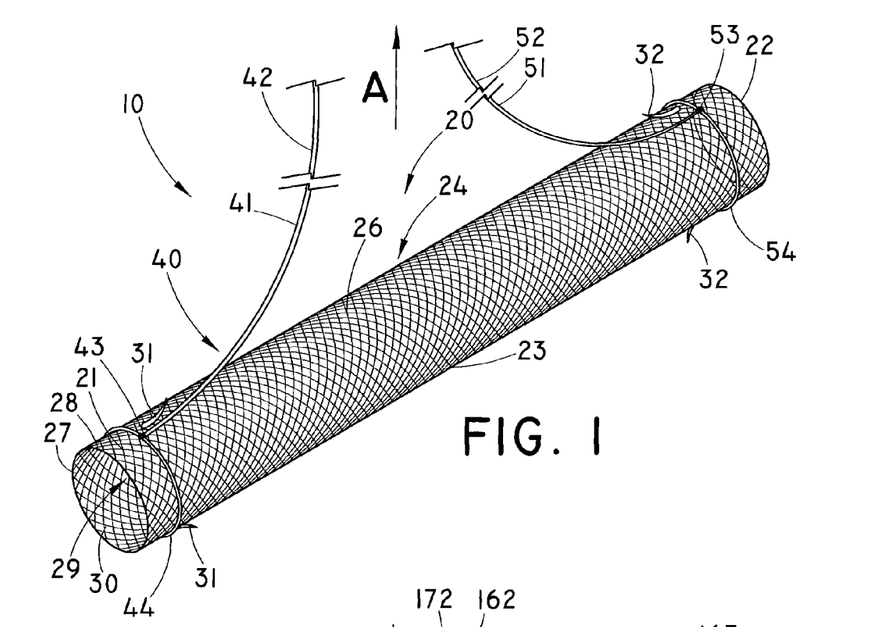
FIG. 1 is a perspective view of one example of a deployment system with a prosthesis being retained in a radially compressed configuration by at least one reduction strand.

FIG. 1 depicts one embodiment of a prosthesis deployment system 10 having a prosthesis 20 and a releasable strand system 40. The prosthesis 20 can have a first outer end 21 and a second outer end 22. The prosthesis 20 can have at least one intermediate portion 24 extending between the first outer end 21 and the second outer end 22. The prosthesis 20 can include a generally tubular graft body 26 having an inner surface 27 and an outer surface 28. The inner surface 27 of the graft body 26 can define a fluid passageway 29 extending longitudinally within the prosthesis 20. The prosthesis 20 further can include a support structure 30 disposed on the inner surface 27 and/or the outer surface 28 of the graft body 26. The prosthesis 20 can be movable between a radially compressed, or delivery, configuration and a radially expanded, or deployed, configuration. Individual portions of the prosthesis 20 may be expandable from the radially compressed configuration independently of other portions of the prosthesis. For example, the first outer end 21 of the prosthesis 20 may be expanded from the radially compressed configuration while the second outer end 22 and/or the intermediate portion 24 of the prosthesis are retained in the radially compressed configuration. Likewise, the second outer end 22 may be expanded while the first outer end 21 and/or the intermediate portion 24 remain compressed. The prosthesis 20 can be balloon expandable; however, it is preferred that the prosthesis be self-expandable. The prosthesis can have a size and shape suitable for at least partial placement within a body vessel, such as an artery or vein, and most particularly, for placement at the site of a vascular trauma as further described herein. The prosthesis may be easily manipulated during delivery to a transected artery or vein during emergency surgery, and particularly, to obtain hemostasis while maintaining blood perfusion.

The prosthesis 20 further can include at least one anchoring member disposed at the first outer end 21 and/or the second outer end 22 thereof. The anchoring member can be attached to the support structure 30 and/or the graft body 26. The anchoring member can be configured to engage a wall of the body vessel to fix the prosthesis 20 to the wall as further described herein. As shown in FIG. 1, the at least one anchoring member can include at least one first anchoring member 31 disposed at the first outer end 21 for fixing the first outer end to a wall of a first vessel portion and at least one second anchoring member 32 disposed at the second outer end 22 for fixing the second outer end to a wall of a second vessel portion. Each of the anchoring members may be configured as a plurality of anchoring members disposed around the entire circumference of the prosthesis. The first and/or second anchoring members 31, 32 can be positioned generally parallel to and/or in abutting contact with the outer surface 28 of the prosthesis 20 to aid in insertion of the prosthesis into the body vessel when the first and/or second outer ends 21, 22, respectively, are in the compressed configuration. The first and/or second anchoring members 31, 32 can be movable to be positioned at an acute angle with respect to the outer surface 28 of the prosthesis 20 to engage the wall of the body vessel when the first and/or second outer ends 21, 22, respectively, are in the expanded configuration. Preferably, the anchoring members provide vessel fixation, while avoiding adverse conditions associated with disturbing the vasa vasorum and/or pressure induced necrosis of the medium muscular arteries of the type that may result from tying ligatures circumferentially around a connector or a vascular conduit. The anchoring members can include various shaped member structures, including barbs, fibers, bristles, or other protruding and penetrating media.

The graft body 26 of the prosthesis 20 can be formed from conventional materials well known in the medical arts. For example, the graft body 26 can be formed from an expanded polytetrafluoroethylene (ePTFE), polytetrafluoroethylene, silicone, polyurethane, polyamide (nylon), as well as other flexible biocompatible materials. The graft body 26 also can be formed from known fabric graft materials such as woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). The graft body 26 also may include a bioremodelable material such as reconstituted or naturally-derived collagenous materials, extracellular matrix material (ECM), submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, and uterine submucosa. One non-limiting example of a suitable remodelable material is SURGISIS® BIODESIGN™ from Cook Medical (Bloomington, Ind.). Another suitable remodelable material is the graft prosthesis material described in U.S. Pat. No. 6,206,931 to Cook et al., which is incorporated herein by reference in its entirety.

The support structure 30 can be a stent having any stent pattern known to one skilled in the art. Non-limiting examples of stent patterns include the Z-STENT® and ZILVER® stent, each available from Cook Medical (Bloomington, Ind.). The support structure 30 can be attached to the graft body 26 by sutures sewn therein, wire, staples, clips, bonding agents, or other methods that may be used to achieve a secure attachment to the graft body. The various components of the support structure 30 can be formed from any biocompatible material known in the art. Non-limiting examples of such materials include a biocompatible metal, such as stainless steel (e.g., 316L SS), titanium, tantalum, nitinol or other shape memory materials, or a high-strength polymer.

Portions of the prosthesis 20 also can include a coating of one or more therapeutic agents along a portion of the graft body 26 and/or the support structure 30. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, and/or genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the prosthesis 20 by any suitable method that permits adequate retention of the agent material and the effectiveness thereof for its intended purpose.

As shown in FIG. 1, the releasable strand system 40 can include at least two reduction strands 41, 51. The first and second reduction strands 41, 51 can have proximal ends 42, 52 and distal ends 43, 53, respectively. Loops 44, 54 can be formed at the distal ends 43, 53, respectively, of the reduction strands 41, 51, which can be releasably coupled to the prosthesis. The reduction strands can have a retaining configuration and a released configuration. In the retaining configuration, the loops 44, 54 can be configured to surround the outer surface 28 at any point along a length of the prosthesis 20 to retain at least the surrounded portion of the prosthesis in the radially compressed configuration. After insertion into the body, the reduction strands can be placed in the released configuration such that the loops no longer surround the prosthesis, and the prosthesis is free to expand. In one example, the reduction strand 41 and/or 51 may be configured such that retracting the proximal end of the respective reduction strand in a direction A may release the respective loop from the prosthesis to allow for expansion thereof. To this end, each of the reduction strands can be disposed along the outer surface 28 of the prosthesis 20 so that the proximal ends of the reduction strands each converge toward the middle of the prosthesis from the outer ends of the prosthesis and toward the direction A. As a result, the proximal ends of the reduction strands can be externally accessible from the middle of the prosthesis as shown in the figures so that removal of the strands occurs from the middle of the prosthesis and toward direction A. One advantage of this arrangement is that during open surgery, the strands can be externally accessible through the trauma pathway formed in the body of the patient along direction A for removal of the strands from the prosthesis to allow for expansion thereof when the outer ends of the prosthesis have been inserted into the end openings of the vessel portions. Alternatively, severing the loop 44 and/or 54 of the respective reduction strand 41 and/or 51 may release the loop from the prosthesis 20 for expansion thereof, and removal of the severed reduction strand can occur along the direction A.

The reduction strands can be applied to the prosthesis in several configurations. In one example, FIG. 1 illustrates the first reduction strand 41 can be positioned at the first outer end 21, and the second reduction strand 51 can be positioned at the second outer end 22 of the prosthesis 20 for compression of the outer ends of the prosthesis. In another example, the first reduction strand may be positioned at the first or second outer end, and the second reduction strand may be positioned axially inward of the outer end along the intermediate portion, as shown, e.g., in FIG. 4. It can be appreciated that two, three, four, five, six or more reduction strands may be provided on the prosthesis.

Figure 2A:
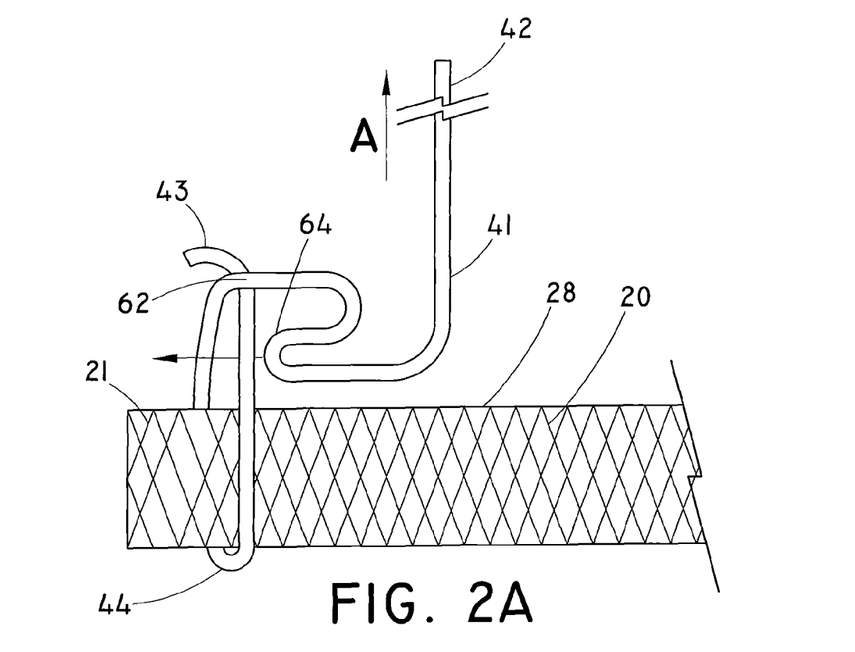
FIGS. 2a-2b are perspective views of one example of placement of a releasable loop of a reduction strand around a prosthesis.
Figure 2B:
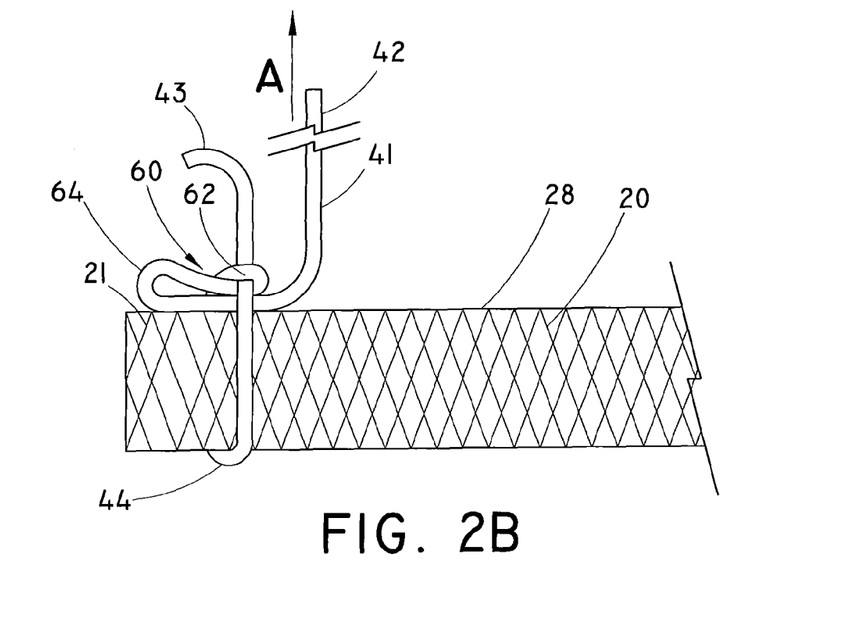
Figure 3A:
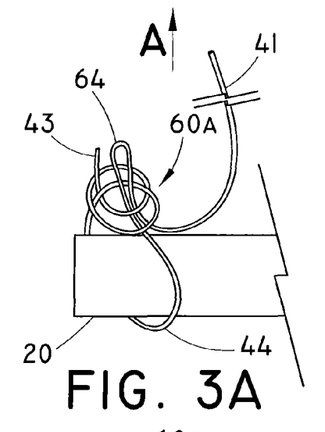
FIGS. 3a-3f are perspective views of additional examples of placement of releasable loops of a reduction strand around a prosthesis.
Figure 3B:
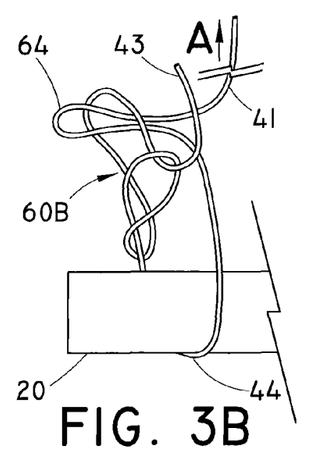
Figure 3C:
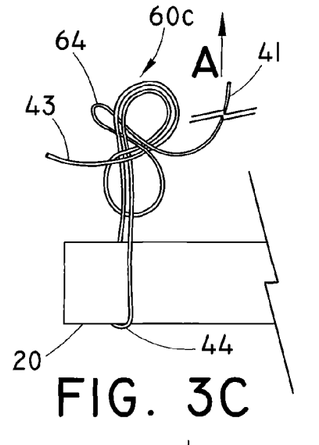
Figure 3D:
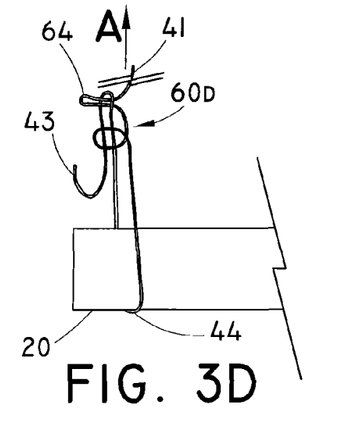
Figure 3E:
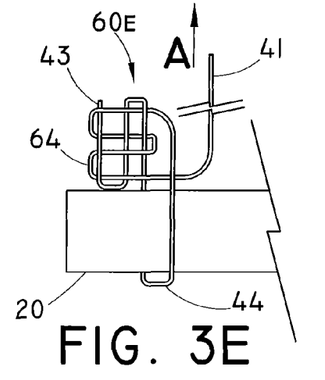
Figure 3F:
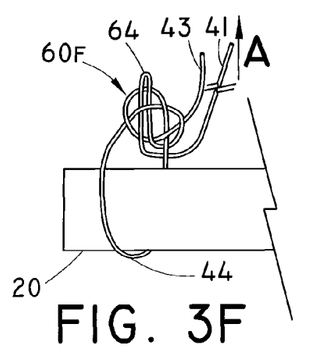

FIGS. 2a-2b and 3a-3f illustrate several examples of releasable knots that can permit the loops to have the retaining configuration and the released configuration. For example, the distal end 43 of the reduction strand 41 can be tied in a knot 60, such as a slippery half hitch as shown in FIG. 2*b*. According to FIG. 2*a*, the distal end 43 can be wrapped around the prosthesis one or more times so that an intersecting portion 62 of the reduction strand can intersect the distal end 43 to form the loop 44. An insertable bight 64 can be formed in the reduction strand 41 near the intersecting portion 62. The bight 64 can be slidably received between the loop 44 of the reduction strand 41 and the outer surface 28 of the prosthesis 20. The bight 64 and the distal end 43 can be pulled tightly for frictional engagement between the bight 64 and the intersecting portion 62 of the strand 41 and the outer surface 28 to form the knot 60. Retraction of the proximal end 42 of the reduction strand 41 can loosen or untie the knot 60 by causing the bight 64 to slide out of engagement between the loop 44 and the outer surface 28, thereby releasing the loop 44 from the first outer end 21 of the prosthesis 20. The knot 60 may have any other suitable configuration known in the art. Non-limiting examples of such knot configurations 60*a*-*f* are illustrated in FIGS. 3*a*-3*f*.

Figure 4:
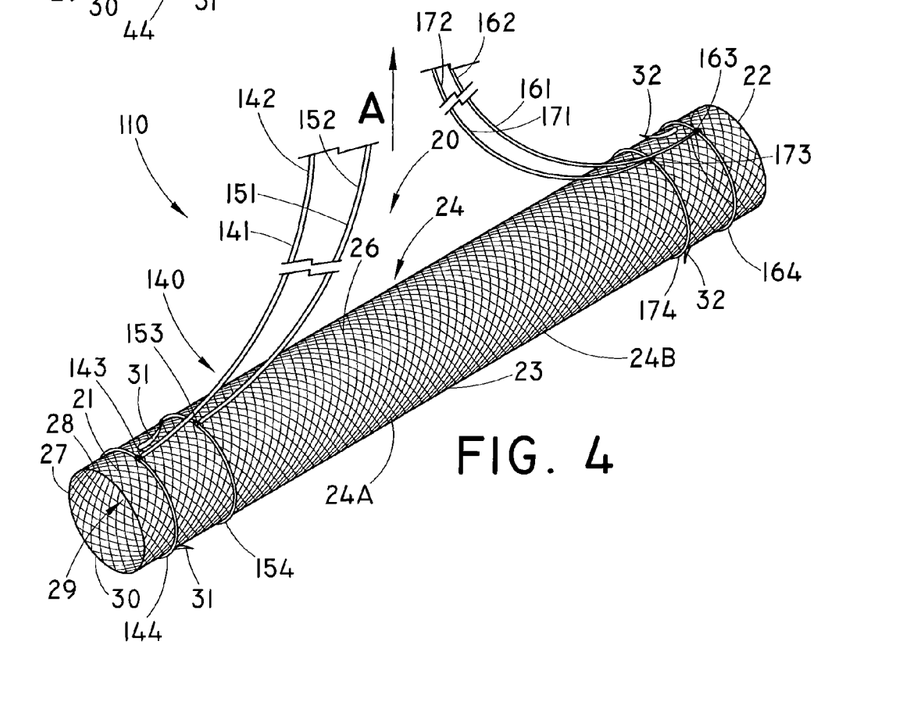
FIG. 4 is a perspective view of another example of a deployment system having a four-strand configuration around a prosthesis.

FIG. 4 depicts another example of a deployment system 110 including the prosthesis 20 and the releasable strand system 140 in a four-strand configuration. The intermediate portion 24 of the prosthesis 20 further can have a first intermediate portion 24*a* located between the first outer end 21 and a midpoint 23 of the prosthesis. Similarly, a second intermediate portion 24*b* can be located between the second outer end 22 and the midpoint 23 of the prosthesis 20. A first loop 144 of a first reduction strand 141 can be configured to surround the outer surface 28 of the prosthesis 20 at the first outer end 21 thereof to retain the first outer end in the radially compressed configuration. A second loop 154 of a second reduction strand 151 can be configured to surround the outer surface 28 of the prosthesis 20 axially inward of the first outer end 21 at the first intermediate portion 24*a* to retain the first intermediate portion in the radially compressed configuration. The first and second loops 144, 154 of the first and second reduction strands 141, 151 can be positioned such that the anchoring members 31 can be positioned substantially between the first loop 144 and the second loop 154. The anchoring members 31 also may be positioned between the first and/or second loop 144, 154 and the outer surface 28 of the prosthesis 20 to retain the anchoring members against the outer surface of the prosthesis for insertion into a body vessel.

The releasable strand system 140 can include a third reduction strand 161 and a fourth reduction strand 171. The third reduction strand 161 can have features identical to those of the first reduction strand 141. The fourth reduction strand 171 can have features identical to those of the second reduction strand 151. The third loop 164 of the third reduction strand 161 can be configured to surround the outer surface 28 of the prosthesis 20 at the second outer end 22 thereof to retain the second outer end in the radially compressed configuration. The fourth loop 174 of the fourth reduction strand 171 can be configured to surround the outer surface 28 of the prosthesis 20 axially inward of the second outer end 22 at the second intermediate portion 24*b* to retain the second intermediate portion in the radially compressed configuration. The third and fourth loops 164, 174 of the third and fourth reduction strands 161, 171 can be positioned such that the anchoring members 32 can be positioned substantially between the third loop 164 and the fourth loop 174. The anchoring members 32 also may be positioned between the third and/or fourth loop 164, 174 and the outer surface 28 of the prosthesis 20 to retain the anchoring members against the outer surface of the prosthesis for insertion into a body vessel.

One of ordinary skill in the art will recognize that the number and placement of the reduction strands may be modified to adapt the deployment system for varying situations. For example, it may be desirable to retain the intermediate portions of the prosthesis in the compressed configuration. In this instance, additional loops disposed around the intermediate portions of the prosthesis may be desirable to retain the intermediate portions of the prosthesis in the radially compressed configurations. For example, additional loops may be desirable when the prosthesis has an increased length or when the support structure of the prosthesis exerts a greater outward radial force. Such modifications are contemplated within the scope of this disclosure.

For further example, a single reduction strand may be configured to engage the outer surface of the prosthesis at multiple positions along a length of the prosthesis. In this instance, the first reduction strand 141 may include a ring (not shown) formed in the first reduction strand at a position between the proximal end 142 and the loop 144. The ring may be formed by wrapping the reduction strand around the outer surface of the prosthesis. The ring may surround the outer surface of the prosthesis to retain the prosthesis in the compressed configuration. Retraction of the proximal end of the first reduction strand may release the loop and then the ring in sequence with a single pulling action. Additional rings may be formed in other reduction strands in similar fashion and with like results. In other instances, it may be desirable for the deployment system further to include a sleeve member (not shown) to supplement the reduction strands in retaining a portion of the prosthesis in the compressed configuration. For example, a sleeve member can be disposed around the outer surface of the prosthesis. The sleeve member can surround substantially all or a portion of the intermediate portion of the prosthesis to retain the intermediate portion in the compressed configuration. The sleeve member can be configured to be removable. To this end, the sleeve member can be configured to peel away from the outer surface of the prosthesis as can be appreciated by those skilled in the art and/or can be constructed of a bioresorbable material. Preferably, the bioresorbable sleeve member can be configured to maintain perfusion during dissolution of the sleeve member.

The reduction strands of the various embodiments can be formed from conventional materials well known in the medical arts. Preferably, the reduction strands may be formed from any engineering fiber that exhibits sufficient flexibility to form the loops and sufficient tensile strength to withstand the radial expansion force exerted by the prosthesis without failure. As a non-limiting example, the reduction strands can be formed from suture materials including, but not limited to, polylactic acid, polyglycolic acid, polydioxane, nylon, polypropylene, or any suitable biocompatible biomaterial such as VICRYL® from Ethicon, Inc. (Somerville, N.J.); or biocompatible metals including, but not limited to, stainless steel and nitinol.

Some prostheses may require that some of the reduction stands are configured for greater radial outward force than the others. Each of the reduction strands may be made of the same material. Alternatively, different reduction strands may be made of different materials. Additionally, different reduction strands may be made having the same or different sizes. For example, the inner reduction strands, such as the second and fourth reduction strands 151, 171, can be configured to have a greater tensile strength compared to the outer reduction strands, such as the first and third reduction strands 141, 161. Such greater tensile strength may be accomplished by forming the second and fourth reduction strands 151, 171 to have a greater cross-sectional area compared to the first and third reduction strands 141, 161. Such greater tensile strength also may be accomplished by forming the second and fourth reduction strands 151, 171 from a different material with superior tensile strength relative to the material used to form the first and third reduction strands 141, 161. Such superior tensile strength may allow the loops of the second and fourth reduction strands 151, 171 to counteract a greater outward radial force than the loops of the first and third reduction strands 141, 161. Thus, the loops of the reduction strands can be positioned along a length of the prosthesis 20 such that a majority of a retaining force required to retain the prosthesis in the radially compressed configuration may be provided by the inner loops, such as the second and fourth loops 154, 174 of the second and fourth reduction strands 151, 171. The outer loops, such as the first and third loops 144, 164 of the first and third reduction strands 141, 161, may provide a relatively small (i.e. with respect to the inner loops) amount of the retaining force required to retain the prosthesis in the radially compressed configuration. In this manner, the outer loops may be released from the prosthesis with less effort than may be required to release the inner loops. This may aid a clinician in releasing the outer loops to anchor the respective outer ends of the prosthesis to a wall of a body vessel portion when the outer loops may be disposed within a lumen of the body vessel portion as further described herein.

Different sizes of reduction strands also may be desirable to aid in removing the reduction strands following expansion of a portion of the prosthesis as described herein. For example, the outer reduction strands, such as the first and third reduction strands 141, 161, may have a lesser cross-sectional area compared to the second and fourth reduction strands 151, 171. Such lesser cross-sectional area may allow the outer reduction strands to slide more efficiently between the outer surface of the prosthesis and the wall of the body vessel after the prosthesis has been expanded to engage the vessel wall. Such lesser cross-sectional area also may allow the outer reduction strands to slide more efficiently between the anchoring members which may be engaged with the vessel wall.

Different types of knots, including those described herein and/or those known in the art, also may be used to secure different loops to impart different amounts of resistance to the expansion force of the prosthesis. This arrangement can facilitate deployment of the prosthesis within a transected body vessel as further described herein. For example, the outer loops, such as the first and third loops 144, 164, can be configured to impart less resistance to the expansion force of the prosthesis and may be more easily released from the prosthesis than the inner loops, such as the second and fourth loops 154, 174. Likewise, the inner loops, such as the second and fourth loops 154, 174, can be configured to impart greater resistance to the expansion force of the prosthesis and may be less easily released from the prosthesis than the outer loops, such as the first and third loops 144, 164. This configuration may allow the first and third loops 144, 164 to be released from the prosthesis 20, e.g., by retracting the proximal ends 142, 162 in the direction A, even though the first and third loops may be inaccessible directly by the clinician, such as when the first and third loops may be within the transected body vessel. This configuration further may allow the second and fourth loops 154, 174 to be released from the prosthesis 20, e.g., by severing the second and fourth loops, when the second and fourth loops may be accessible directly by the clinician. In other words, the second and/or fourth loops 154, 174 may be configured to bear a majority of the radial expansion force exerted by the prosthesis 20 so that the first and/or third loops 144, 164 may be more easily removed from the prosthesis when the first and/or second ends 21, 22 of the prosthesis may be disposed within a transected body vessel.

The first reduction strand 141 can be slidably received between the second loop 154 of the second reduction strand 151 and the outer surface 28 of the prosthesis 20. Such a configuration may allow a portion of the first reduction strand to be placed adjacent, or to lie against, the outer surface 28 of the prosthesis 20. The proximal end 142 of the first reduction strand 141 and the proximal end 152 of the second reduction strand 151 can be disposed in a retraction zone that is proximate to a plane perpendicular to a longitudinal axis of the prosthesis 20 and passing through the midpoint 23 of the prosthesis for more efficient access to the proximal ends 142, 152. The retraction zone may be externally accessible within a space between two portions of a transected body vessel when the prosthesis is employed to bridge the vessel portions. Each of the reduction strands can be disposed exterior to the prosthesis so that the proximal ends of all of the reduction strands converge toward the midpoint 23 of the prosthesis in the direction A so that the proximal ends of the reduction strands are externally accessible from the middle of the prosthesis during open surgery. To this end, more efficient access to the proximal ends of the reduction strands may reduce the time required for the clinician to remove the reduction strands to allow the prosthesis to expand during surgery. Similarly, the third reduction strand 161 can be disposed to pass between the fourth loop 174 of the fourth reduction strand 171 and the outer surface 28 of the prosthesis 20 in like fashion and with like result.

The proximal ends 142, 162 of the outer strands, such as the first and third reduction strands 141, 161, respectively, can be coupled to one another such that the first and third loops 144, 164 can be released with a single retracting action in the direction A as described herein. Likewise, the proximal ends 152, 172 of the inner strands, such as the second and fourth reduction strands 151, 171, respectively, can be coupled to one another such that the second and fourth loops 154, 174 can be released with a single retracting action in the direction A. Optionally, the proximal ends 142, 152 of the strands retaining one side of the prosthesis, such as the first and second reduction strands 141, 151, respectively, can be coupled to one another such that the first and second loops 144, 154 can be released with a single retracting action in the direction A as described herein. Likewise, the proximal ends 162, 172 of the strands retaining the other side of the prosthesis, such as the third and fourth reduction strands 161, 171, respectively, can be coupled to one another such that the third and fourth loops 164, 174 can be released with a single retracting action in the direction A. Additionally, all of the proximal ends of the first, second, third, and fourth reduction strands can be coupled to one another such that all of the loops can be released with a single retracting action in the direction A. The proximal ends of the reduction strands can be disposed proximate to the retraction zone near the plane passing through the midpoint of the prosthesis in the direction A to aid in accessing the proximal ends of the reduction strands for removal from the patient's body.

It is further contemplated that the reduction strands can be coupled to one another to permit a sequential expansion of the prosthesis in a desired sequence with one, two, three, four or more retracting actions. For example, a single retracting action can release the outer loops first and then the inner loops. In another example, a first retracting action can release the first outer loop and then the first inner loop, while a second retracting action can release the second outer loop and then the second inner loop. In another example, a first retracting action can release the first outer loop, a second retracting action can release the second outer loop, and a third retracting action can release the first and second inner loops.

Although the system has been described in connection with its primary intended use for repair of vascular trauma, those skilled in the art will appreciate that the system may also be used to repair other traumatic conditions. Non-limiting examples of such conditions include aneurysms, such as abdominal aorta aneurysms, and surgery for tumor removal.

Figure 5A:
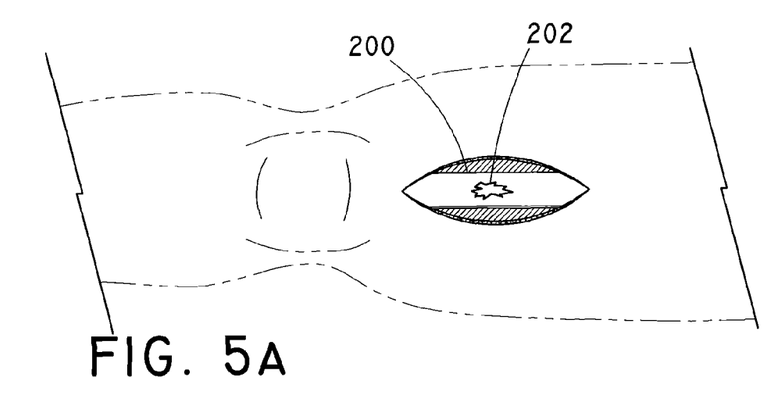
FIGS. 5a-5g illustrate a method of connecting two vessel portions of a transected body vessel with one example of a deployment system.
Figure 5B:
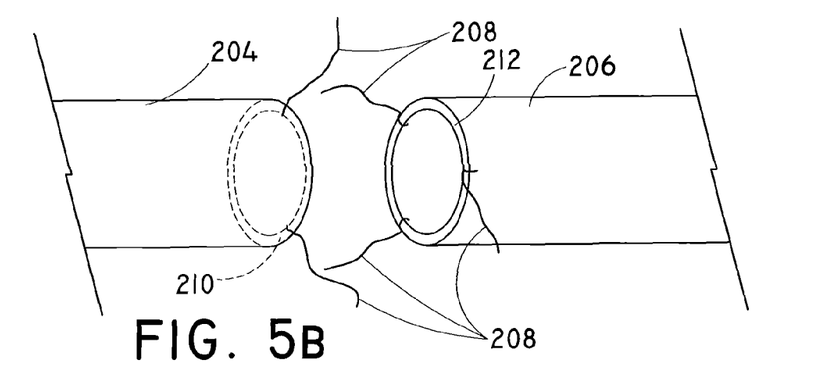

FIGS. 5a-5g illustrate a method of treating a body vessel 200, such as connecting two vessel portions of a transected vessel. In FIG. 5a, the body vessel 200 may be found, for example, in the leg of a patient having been subjected to a traumatic episode resulting in a portion 202 of the body vessel 200 being torn away or otherwise severely damaged. Pre-surgery preparation may be applied to the leg, and a trauma pathway may be formed therein to gain access to the body vessel 200 and the damaged portion 202 thereof and to form the retraction zone. In FIG. 5b, after clamping the body vessel 200 on both ends of the portion 202 to restrict blood flow temporarily, the body vessel 200 can be cut or transected by the clinician into two portions 204, 206. The transection may be at the damaged portion 202 of the body vessel 200 or as far away as necessary from the damaged portion to remove unhealthy portions of the body vessel or unrepairable portions of the body vessel. Sutures 208 can be attached to end openings 210, 212 of the body vessel portions 204, 206 to keep them fixed in place and open to facilitate insertion of the prosthesis 20. Forceps may also be used in a similar manner. Any number of sutures 208 can be used to retain the end openings 210, 212 in the open position, although triangulation sutures can be sufficient, with each suture being about 120 degrees apart from the adjacent suture. The prosthesis 20 is selected to have a radial expanded cross-section and a longitudinal length sufficient to bridge the body vessel portions 204, 206 and fit radially therein.

Figure 5C:
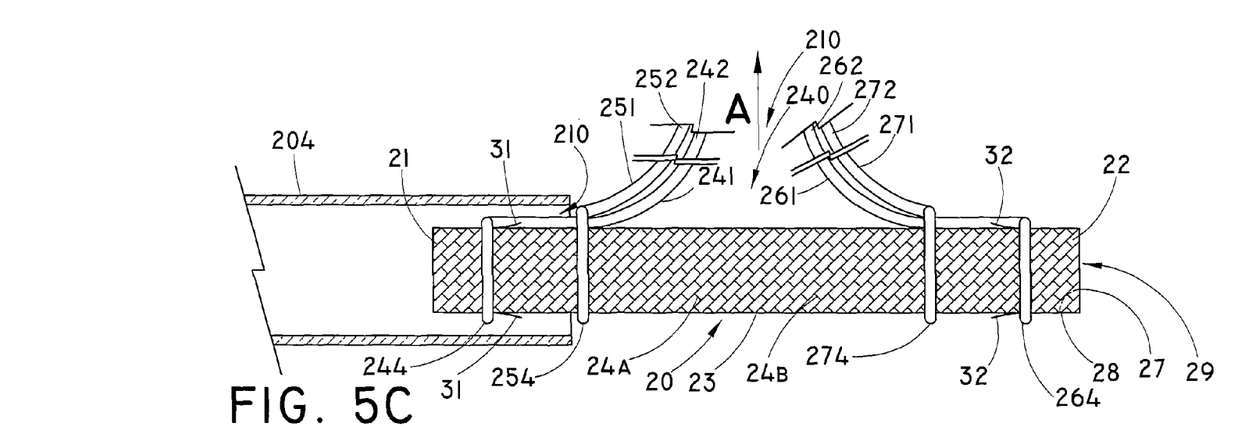
Figure 5D:
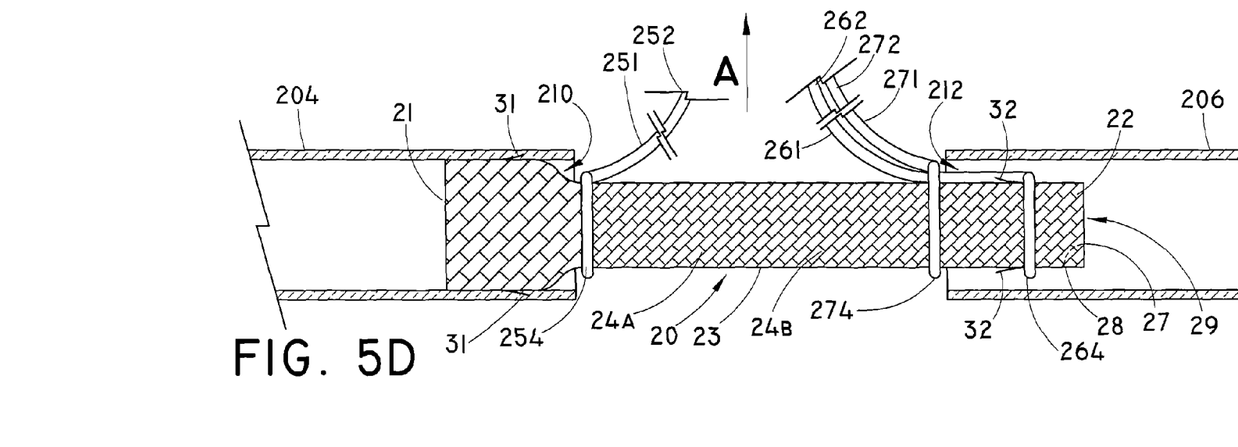

FIG. 5c depicts the prosthesis 20 held in the radially compressed, delivery configuration by at least one loop of the one or more reduction strands. The loops can be configured to be released from the prosthesis 20 as described herein and removed such that no portion of any of the reduction strands remains in the patient's body following treatment. The prosthesis may be crimped into the radially compressed, delivery configuration by a stent compressor as known in the art. The compressed prosthesis may be cooled to a reduced temperature to aid in tying the loops around the prosthesis. The reduced temperature may be a temperature below a recovery temperature of the material used to form the support structure 30 of the prosthesis 20. In FIG. 5c, with the reduction strands in the retaining configuration around the prosthesis, the first outer end 21 of the prosthesis 20 can be inserted through the end opening 210 into the first vessel portion 204 by a sufficient distance for the purposes of anchoring. The loop 244 of the first outer reduction strand 241 may be positioned within the lumen of the first vessel portion 204 as shown in FIG. 5c. It is preferred that the first vessel portion initially selected be the non-blood supplying vessel portion. The first vessel portion 204 may be manually pulled over the first outer end of the prosthesis. After insertion of the first outer end, the proximal end 242 of the first outer reduction strand 241 can be retracted by the clinician in the direction A to release the respective loop 244 from the first outer end of the prosthesis, as described herein. This can permit expansion and purchase of the first outer end of the prosthesis along the wall of the vessel portion 204, as shown in FIG. 5d. Additionally, the anchoring members 31 can engage the wall of the first vessel portion 204 to fix the first outer end of the prosthesis in place relative to the vessel portion. The first outer reduction strand 241 can be withdrawn from the patient's body.

Figure 5E:
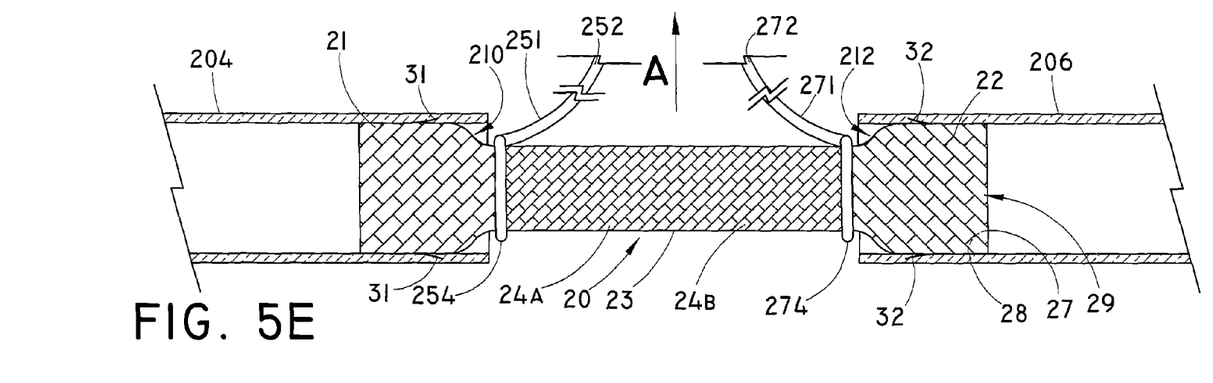

Also in FIG. 5d, the prosthesis 20 then can be manipulated to introduce the second outer end 22 of the prosthesis 20 through the end opening 212 into the second vessel portion 206 by a sufficient distance for the purposes of anchoring. The loop 264 of the second outer reduction strand 261 may be positioned within the lumen of the second vessel portion 206 as shown in FIG. 5d. The second vessel portion 206 may be manually pulled over the second outer end 22 of the prosthesis 20. After insertion of the second outer end of the prosthesis, the proximal end 262 of the second outer reduction strand 261 can be retracted in the direction A to release the respective loop 264 from the second outer end 22 of the prosthesis 20, as described herein. This can permit expansion and purchase of the second outer end 22 of the prosthesis 20 along the wall of the second vessel portion 206 as shown in FIG. 5e. Additionally, the anchoring members 32 can engage the wall of the second vessel portion 206 to fix the second outer end 22 of the prosthesis 20 in place relative to the second vessel portion. The second outer reduction strand 261 can be withdrawn from the patient's body. It is contemplated that the first and second outer ends of the prosthesis may be inserted within the end openings of the vessel portions before retracting the first and second outer reduction strands sequentially or together at once.

Although the system shown in FIGS. 5c-5f includes first and second inner strands 251, 271, it can be appreciated by those skilled in the art that the system can be fully deployed after the steps shown in FIG. 5e. The inclusion of the first and second inner strands 251, 271 may aid a clinician in deploying the prosthesis within the first and/or second vessel portions. For example, when at least a portion of the retaining force required to retain the prosthesis in the compressed configuration may be provided by the first and/or second inner strands, the first and/or second outer strands may be allowed to provide less retaining force, and thus, less effort may be required to release the first and/or second outer loops. This may aid a clinician by reducing the effort required to release the first and/or second outer loops when the loops may be disposed within the lumens of the vessel portions and by allowing the first and/or second outer strands to be removed from the vessel portions before the prosthesis may be fully expanded. When the first and second inner strands 251, 271 are present, the loops 254, 274 of the first and second inner reduction strands may be positioned externally of the first and second vessel portions 204, 206 in a space between the first and second vessel portions as shown in FIGS. 5d-5e. The loop 254 of the first inner reduction strand 251 can be released from the first intermediate portion 24a of the prosthesis 20. For example, the loop can be released by any suitable means such as severing the loop 254 or retracting the proximal end 252 of the first inner reduction strand 251 in the direction A as described herein. This can permit expansion of the first intermediate portion 24a of the prosthesis 20. The first vessel portion 204 now can be sealably engaged with the first outer end 21 of the prosthesis 20. The first inner reduction strand 251 can be withdrawn from the patient's body. Likewise, the loop 274 of the second inner reduction strand 271 can be released from the second intermediate portion 24b of the prosthesis 20 by any suitable means as described herein. This can permit expansion of the second intermediate portion 24b of the prosthesis 20. The second vessel portion 206 now can be sealably engaged with the second outer end 22 of the prosthesis 20. The second inner reduction strand 271 can be withdrawn from the patient's body. It is contemplated that the first inner reduction strand can be released before or after the vessel insertion of the second outer end of the prosthesis. Further, retraction of the first and second inner reduction strands can occur sequentially relative to one another, together at once, sequentially relative to the respective first and second outer reduction strands, or together at once with the respective first and second outer reduction strands as described herein.

Figure 5F:
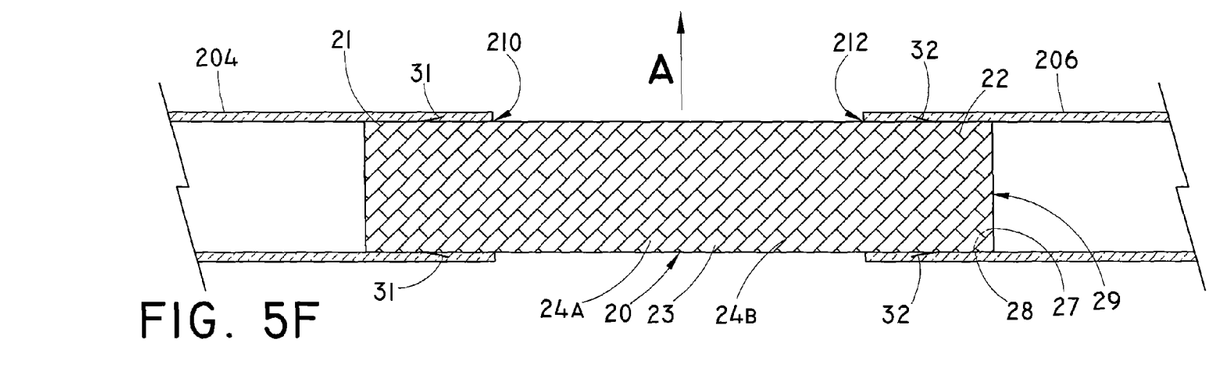
Figure 5G:
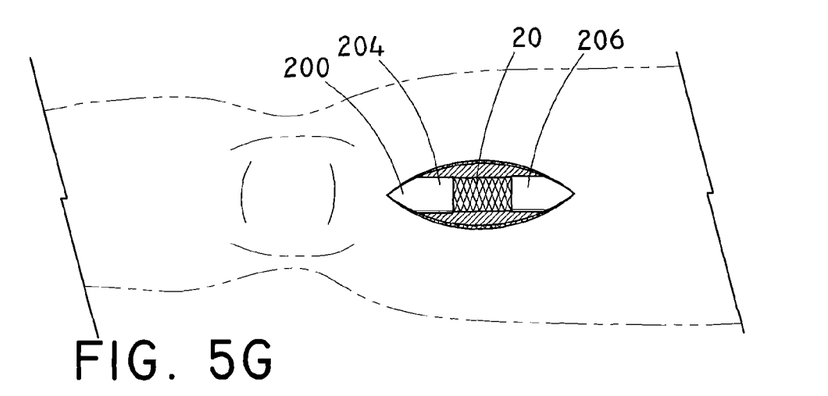

Accordingly, in FIG. 5f, the prosthesis 20 can be fully deployed to bridge the first and second vessel portions 204, 206 of the transected body vessel 200. A conduit for blood flow may be formed by the fluid passageway 29 of the prosthesis 20 in communication with interior lumens of the first and second vessel portions 204, 206. The sutures 208 can be removed. Preferably, portions of the outer surface 28 of the prosthesis 20 can sealably engage with the luminal walls of the body vessel portions 204, 206 to inhibit leakage of blood and to force blood to flow throughout the body vessel 200 during emergency surgery, and particularly to obtain hemostasis while maintaining blood perfusion. FIG. 5g shows the prosthesis 20 deployed and connecting the body vessel portions 204, 206 within the leg of the patient. The prosthesis 20 can be adapted for permanent placement within the patient, thereby obviating a need for subsequent surgical intervention.

It can be appreciated by those skilled in the art that specific features of each embodiment of the deployment system are interchangeable among the device embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments, and may be combined with each other and/or with currently-known or future-developed technologies while remaining within the scope of the claims presented here. It is therefore intended that the foregoing detailed description be regarded as illustrative rather than limiting. And it should be understood that the following claims, including all equivalents, are intended to define the spirit and scope of this invention.

I claim:

1. A system for connection between two vessel portions during open surgery, the system comprising:
    a prosthesis movable between a compressed configuration and an expanded configuration, the prosthesis having a first outer end, a second outer end, and an intermediate portion extending therebetween, each of the first and second outer ends and the intermediate portion independently retainable in the compressed configuration and movable therefrom to the expanded configuration; and
    a first strand, a second strand, and a third strand each having a proximal end and a distal end, the first strand comprising a first releasable loop at the distal end thereof, the second strand comprising a second releasable loop at the distal end thereof, and the third strand comprising a third releasable loop at the distal end thereof, the first releasable loop surrounding the first outer end of the prosthesis to retain the first outer end of the prosthesis in the compressed configuration, the second releasable loop surrounding the second outer end of the prosthesis to retain the second outer end of the prosthesis in the compressed configuration, and the third releasable loop surrounding the intermediate portion of the prosthesis to retain the intermediate portion of the prosthesis in the compressed configuration,
    wherein at least one of the first and second releasable loops is configured to be removed in response to retraction of the proximal end of the corresponding strand from external to the prosthesis, to allow for expansion of the corresponding first or second portion of the prosthesis to the expanded configuration to engage a vessel portion,
    wherein at least one of the first and second strands comprises a tensile strength less than a tensile strength of the third strand such that the third strand is configured to withstand a greater proportion of an outward radial force exerted by the prosthesis than the first or second strand when the first and second outer ends and the intermediate portion of the prosthesis are held in the compressed configuration.

2. The system of claim 1, wherein the intermediate portion of the prosthesis comprises a first intermediate portion and a second intermediate portion axially spaced from the first intermediate portion, the system further comprising a fourth strand having a proximal end, a distal end, and a fourth releasable loop at the distal end thereof,
    wherein the third releasable loop surrounds the first intermediate portion of the prosthesis to retain the first intermediate portion of the prosthesis in the compressed configuration, and the fourth releasable loop surrounds the second intermediate portion of the prosthesis to retain the second intermediate portion of the prosthesis in the compressed configuration.

3. The system of claim 2, wherein the prosthesis comprises a first anchoring member proximate the first outer end thereof and a second anchoring member proximate the second outer end thereof, each of the anchoring members configured to affix to a wall of the vessel portion, wherein the first and third releasable loops are positioned such that the first anchoring member is disposed between the first and third releasable loops, and the second and fourth releasable loops are positioned such that the second anchoring member is disposed between the second and fourth releasable loops.

4. The system of claim 2, wherein each of the first, second, third, and fourth strands is disposed exterior to the prosthesis, and the proximal end of each of the strands converges toward a middle of the prosthesis so that each of the proximal ends is externally accessible from the middle of the prosthesis.

5. The system of claim 2, wherein the first and second releasable loops are secured by respective first and second knots configured to be released in response to retraction of the respective proximal ends to allow for expansion of the corresponding first and second portions of the prosthesis to the expanded configuration to engage a vessel portion, and the third and fourth releasable loops are configured to be severed to allow for expansion of the corresponding first and second intermediate portions of the prosthesis to the expanded configuration.

6. The system of claim 1, wherein the first and second strands are disposed exterior to the prosthesis so that the proximal ends of the first and second strands converge toward a middle of the prosthesis and are externally accessible from the middle of the prosthesis.

7. The system of claim 1, wherein the proximal ends of the first and second strands are coupled to one another such that a single retraction of the coupled proximal ends allows for expansion of both of the first and second outer ends of the prosthesis.

8. A system for connection between first and second vessel portions of a transected body vessel during open surgery, the system comprising:

a prosthesis having a first outer end and a second outer end, and a first intermediate portion and a second intermediate portion therebetween, the prosthesis being movable between a compressed configuration and an expanded configuration; and a first outer strand, a second outer strand, a first inner strand, and a second inner strand each comprising a proximal end and a distal end, and a releasable loop at the distal end thereof, the releasable loop of the first outer strand surrounding the first outer end of the prosthesis to retain the first outer end in the compressed configuration, the releasable loop of the first inner strand surrounding the first intermediate portion of the prosthesis to retain the first intermediate portion in the compressed configuration, the releasable loop of the second outer strand surrounding the second outer end of the prosthesis to retain the second outer end in the compressed configuration, and the releasable loop of the second inner strand surrounding the second intermediate portion of the prosthesis to retain the second intermediate portion in the compressed configuration, the releasable loop of each of the first outer strand, the first inner strand, the second outer strand, and the second inner strand being independently releasable to allow for expansion of the respective first outer end, first intermediate portion, second outer end, and second intermediate portion of the prosthesis;

wherein each of the first outer strand, the first inner strand, the second outer strand, and the second inner strand is disposed external to the prosthesis so that the proximal ends of the strands converge toward a middle of the prosthesis and are externally accessible from the middle of the prosthesis, and the releasable loops of the first and second outer strands are configured to be positioned within said first and second vessel portions, respectively, and the releasable loops of the first and second inner strands are configured to be positioned externally of the first and second vessel portions in a space between the first and second vessel portions, wherein the releasable loop of each of the first and second inner strands is secured by a knot configured to be released in response to retraction of the proximal end of the respective strand from external to the prosthesis to allow for expansion of the corresponding first or second intermediate portion of the prosthesis to the expanded configuration, and the proximal ends of the first and second inner strands are coupled to one another such that a single retraction of the coupled proximal ends allows for expansion of both of the first and second intermediate portions of the prosthesis, wherein the first and second outer strands comprise a tensile strength less than a tensile strength of the first and second inner strands such that the first and second inner strands are configured to withstand a greater proportion of an outward radial force exerted by the prosthesis than the first and second outer strands.

9. The system of claim 8, wherein the releasable loop of each of the first and second outer strands is secured by a knot configured to be released in response to retraction of the proximal end of the corresponding strand from external to the prosthesis to allow for expansion of the corresponding first or second outer end of the prosthesis to the expanded configuration to engage a vessel portion.

10. The system of claim 9, wherein the proximal ends of the first and second outer strands are coupled to one another such that a single retraction of the coupled proximal ends allows for expansion of both of the first and second outer ends of the prosthesis.

11. The system of claim 8, wherein the prosthesis comprises a first anchoring member proximate the first outer end thereof configured to affix to a wall of the first vessel portion and a second anchoring member proximate the second outer end thereof configured to affix to a wall of the second vessel portion, wherein the releasable loops of the first outer strand and the first inner strand are positioned such that the first anchoring member is disposed between the releasable loops of the first outer strand and the first inner strand, and the releasable loops of the second outer strand and the second inner strand are positioned such that the second anchoring member is disposed between the releasable loops of the second outer strand and the second inner strand.

12. The system of claim 8, wherein the releasable loops of the first and second inner strands are configured to be severed from external to the prosthesis to allow for expansion of the corresponding intermediate portions of the prosthesis to the expanded configuration.

13. A system for connection between two vessel portions during open surgery, the system comprising:

a prosthesis movable between a compressed configuration and an expanded configuration, the prosthesis having a first outer end, a second outer end, and an intermediate portion extending therebetween, each of the first and second outer ends and the intermediate portion independently retainable in the compressed configuration; and a first strand, a second strand, and a third strand each having a proximal end and a distal end, the first strand comprising a first releasable loop at the distal end thereof, the second strand comprising a second releasable loop at the distal end thereof, and the third strand comprising a third releasable loop at the distal end thereof, the first releasable loop surrounding the first outer end of the prosthesis to retain the first outer end of the prosthesis in the compressed configuration, the second releasable loop surrounding the second outer end of the prosthesis to retain the second outer end of the prosthesis in the compressed configuration, and the third releasable loop surrounding the intermediate portion of the prosthesis to retain the intermediate portion of the prosthesis in the compressed configuration, wherein at least one of the first and second strands comprises a tensile strength less than a tensile strength of the third strand such that the third strand is configured to withstand a greater proportion of an outward radial force exerted by the prosthesis than the first or second strand when the first and second outer ends and the intermediate portion of the prosthesis are held in the compressed configuration;

wherein at least one of the first and second releasable loops is configured to be removed in response to retraction of the proximal end of the corresponding strand from external to the prosthesis, to allow for expansion of the corresponding first or second portion of the prosthesis to the expanded configuration to engage a vessel portion.

14. The system of claim 13, wherein the intermediate portion of the prosthesis comprises a first intermediate portion and a second intermediate portion axially spaced from the first intermediate portion, the system further comprising a fourth strand having a proximal end, a distal end, and a fourth releasable loop at the distal end thereof, wherein the third releasable loop surrounds the first intermediate portion of the prosthesis to retain the first intermediate portion of the prosthesis in the compressed configuration, and the fourth releasable loop surrounds the second intermediate portion of the prosthesis to retain the second intermediate portion of the prosthesis in the compressed configuration.

15. The system of claim 14, wherein the prosthesis comprises a first anchoring member proximate the first outer end thereof and a second anchoring member proximate the second outer end thereof, each of the anchoring members configured to affix to a wall of the vessel portion, wherein the first and third releasable loops are positioned such that the first anchoring member is disposed between the first and third releasable loops, and the second and fourth releasable loops are positioned such that the second anchoring member is disposed between the second and fourth releasable loops.

16. The system of claim 14, wherein each of the first, second, third, and fourth strands is disposed exterior to the prosthesis, and the proximal end of each of the strands converges toward a middle of the prosthesis so that each of the proximal ends is externally accessible from the middle of the prosthesis.

17. The system of claim 13, wherein the proximal ends of the first and second strands are coupled to one another such that a single retraction of the coupled proximal ends allows for expansion of both of the first and second outer ends of the prosthesis.

* * * * *